United States Patent [19]

Nosaka et al.

[11] 4,133,642

[45] Jan. 9, 1979

[54] PIPETTING APPARATUS FOR AUTOMATIC ANALYZER

[75] Inventors: Shozo Nosaka, Tokyo; Masahiro Yamamoto, Fuji, both of Japan

[73] Assignee: Terumo Corporation, Tokyo, Japan

[21] Appl. No.: 885,120

[22] Filed: Mar. 10, 1978

[51] Int. Cl.² .................. G01N 33/16; G01N 1/14
[52] U.S. Cl. ................ 422/67; 73/425.4 R; 360/1; 364/415; 364/497; 422/100
[58] Field of Search ............ 23/259, 253 R; 364/415, 364/416, 497; 360/1; 73/425.4 R

[56] References Cited

U.S. PATENT DOCUMENTS

| | | | |
|---|---|---|---|
| 3,350,946 | 11/1967 | Isreeli | 23/253 UX |
| 3,565,582 | 2/1971 | Young | 23/253 X |
| 3,680,967 | 8/1972 | Engelhardt | 23/253 X |
| 3,684,453 | 8/1972 | Lartigue et al. | 23/259 X |
| 3,754,872 | 8/1973 | Zauft | 23/259 X |
| 3,778,790 | 12/1973 | Prost et al. | 23/253 X |
| 3,854,879 | 12/1974 | Figueroa | 23/259 X |
| 3,916,157 | 10/1975 | Roulette et al. | 23/259 X |
| 3,917,455 | 11/1975 | Bak et al. | 23/259 X |

*Primary Examiner*—R.E. Serwin
*Attorney, Agent, or Firm*—Bacon & Thomas

[57] ABSTRACT

A read-write head writes data relative to a patient in a magnetic tape disposed on a sample supply container and reads out the written data. The read data are displayed on a display device to check the data for correctness. The sample supply container in which the data have been written is delivered to a pipetting device, which distributes a sample in the sample supply container to a sample receptacle. At this time, the data stored in the magnetic tape of the sample supply container are read out by a magnetic head, and written in a magnetic tape attached to the sample receptacle. The data written in the magnetic tape of the sample receptacle are read out by a magnetic head, and compared with the data stored in the magnetic tape of the sample supply container, and then the sample is pipetted.

5 Claims, 7 Drawing Figures

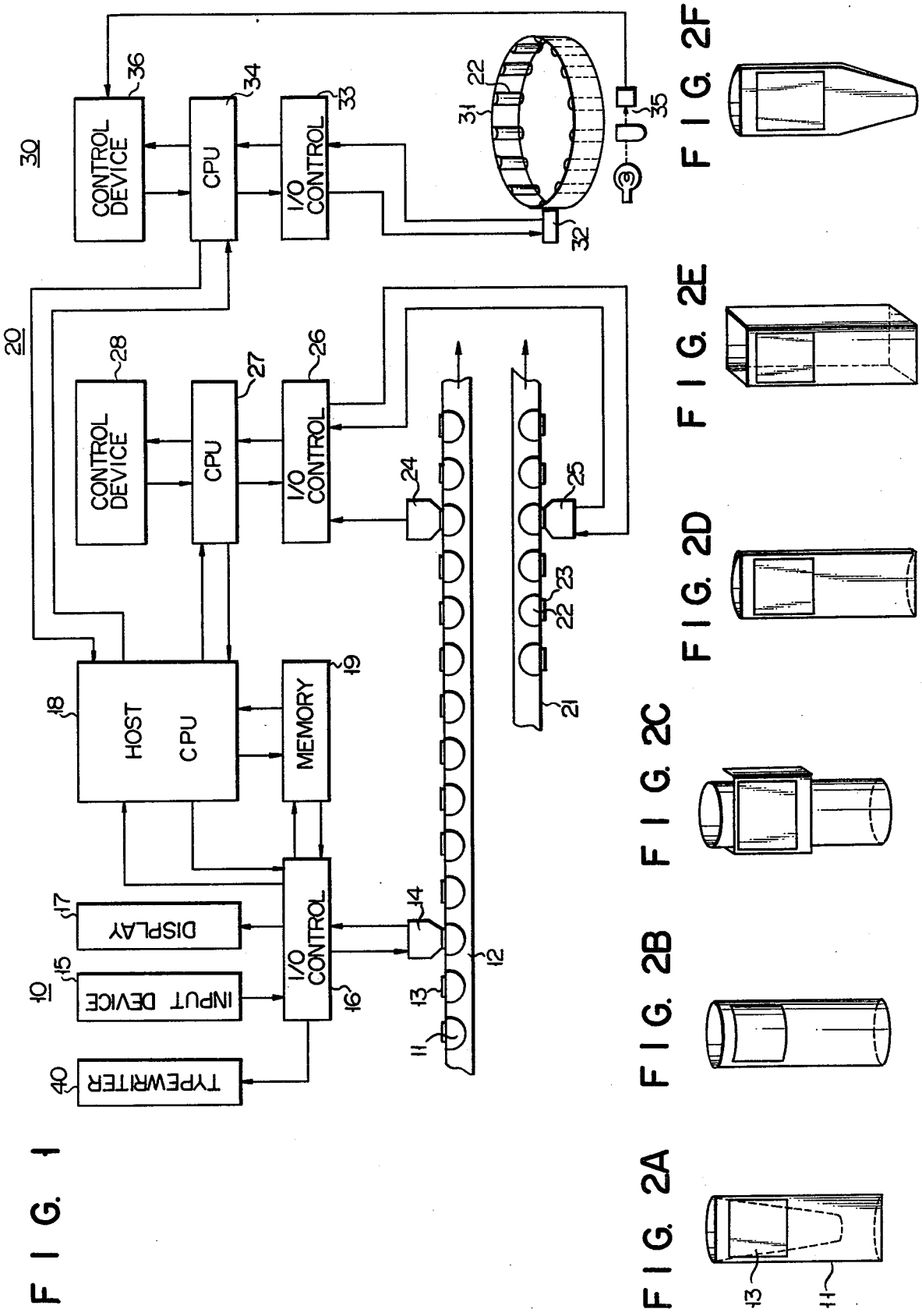

PIPETTING APPARATUS FOR AUTOMATIC ANALYZER

BACKGROUND OF THE INVENTION

This invention relates to a pipetting apparatus for an automatic analyzer to analyze samples, such as body fluids, automatically.

Recently, the number of samples managed in a biochemical analysis in a laboratory of a hospital, clinic or the like has remarkably been increasing. Then, in order to improve the efficiency of inspective operation as a whole, automatic analyzers have come into use. In the analysis of samples, a single sample would be subjected to various inspections, so that the sample should be distributed to a plurality of sample receptacles, a plurality of pipetted samples being separately analyzed for varied analysis data.

Hereupon, in pipetting each of varied samples collected from a number of patients to a number of containers and individually analyzing the pipetted samples, the sample obtained after the pipetting need be precisely identical with the sample before the pipetting. There have not, however, been obtained any effective means for precisely maintaining such identity yet.

SUMMARY OF THE INVENTION

Accordingly, an object of this invention is to provide a pipetting apparatus capable of precisely maintaining the identity of samples before and after pipetting.

According to the invention, there is provided a pipetting apparatus in which sample supply containers and sample receptacles are each provided with a recording medium, and pipetting is conducted after sample data stored in the recording medium of each sample supply container is transmitted to and stored in each corresponding sample receptacle and the identity of the data stored in the recording media of both containers is confirmed.

BRIEF DESCRIPTION OF THE DRAWINGS

FIG. 1 is a block circuit diagram of a pipetting apparatus of an automatic analyzer according to an embodiment of this invention; and FIGS. 2A to 2F are perspective views of various types of sample supply containers and sample receptacles used with the pipetting apparatus of FIG. 1.

DETAILED DESCRIPTION OF THE PREFERRED EMBODIMENT

Referring now to FIG. 1, a plurality of sample supply containers 11 receiving samples collected from a number of patients, such as blood or other body fluids, are moved in the direction indicated by an arrow by means of a conveyor 12. Each sample supply container 11, as shown in FIG. 2A, is an elongated container having a flat side affixed by a recording medium, e.g. magnetic tape 13. A magnetic head 14 is disposed so as to come in contact with the magnetic tape 13 of the sample supply container 11. The magnetic head 14 is composed of a read-write head which has both writing and reading functions. By means of this read-write head 14, the data on a sample held by the sample supply container 11, such as patient code, sample number, sample-collecting time, collector code, sample conditions, etc., are stored in the magnetic tape 13 of the container 11. In doing this, the data are supplied to the read-write head 14 from an input device, for example, keyboard 15 through an I/O control 16, for example. The data written in the magnetic tape 13 are immediately read by the same read-write head 14, and supplied through the I/O control 16 to a display device 17, where it is determined whether or not the data written in the magnetic tape 13 of the sample supply container are correct. If the written data prove to be correct, they are supplied to a host CPU 18 and/or a memory 19. The sample supply container 11 in which the data have been written is carried to a pipetting device 20. This pipetting device 20 has a sample receptacle conveyor 21 which moves in the same direction with the sample supply container conveyor 12, supporting a plurality of sample receptacles 22 opposite to the sample supply containers 11 supported by the conveyor 12. Each sample receptacle 22, like the sample supply container 11, is an elongated container with a magnetic tape 23, as shown in FIG. 2A. Further, the pipetting device 20 is provided with a magnetic head 24 to come in contact with the magnetic tape 13 of the carried sample supply container 11 and a read-write head 25 to come in contact with the magnetic tape 23 of the sample receptacle 22.

The sample data stored in the magnetic tape 13 of the sample supply container 11 conveyed to the pipetting device 20 are read out by the magnetic head 24. The read sample data are supplied to the read-write head 25 through the I/O control 26, and written in the magnetic tape 23 of the sample receptacle 22. The data written in the sample receptacle 22 are immediately read by the same read-write head 25, and supplied to a CPU 27 through the I/O control 26. In this CPU 27, the sample data for the sample supply container 11 read out by the magnetic head 24 are compared with the sample data for the sample receptacle 22. If both sample data are identical, then a pipetting control device 28 controls a distribution mechanism (not shown) in accordance with pipetting information including e.g. amount of pipetting sample and pipetting speed and applied to the input of the CPU 18 by an input device such as keyboard, thereby inducing the mechanism to perform automatic pipetting.

In the pipetting device 20 the sample receptacle 22 supplied with the sample is delivered to an automatic analyzer 30, where it is held up by a sample tray 31. In this automatic analyzer 30 the sample data in the magnetic tape of the sample receptacle 22 sustained by the sample tray 31 are read by a read-write head 32, and delivered to a CPU 34 through an I/O control 33. The pipetted sample in the sample receptacle 22 is analyzed by an optical analyzer 35, for example, and the results of such analysis are supplied to an analysis control device 36 including a decoder. The analysis data obtained by means of the analysis control device 36 are supplied to the CPU 34, where they are transmitted to the host CPU 18 with the corresponding sample data that have previously been read. The data transmitted to the host CPU 18 are delivered through the I/O control 16 to e.g. a typewriter unit 40, where they are typewritten as final data.

Thus, according to the pipetting apparatus of this invention, the sample data recorded in the recording medium attached to the sample supply container are recorded in the recording medium attached to the sample receptacle, and pipetting is conducted while confirming the identity of these recorded data with the sample data in the sample supply container by computer control, so that the precise identity of the sample in the supply container with the sample in the sample receptacle may be always ensured.

Although in the above embodiment pipetting is conducted for each sample supply container, it may also be conducted at one time for several sample supply containers. In this case, a plurality of sample supply containers and sample receptacles are moved at once, sample information for each sample supply container is read and quickly written in the recording medium of its corresponding sample receptacle in the course of such movement.

Although the magnetic tape is used for the recording medium in the above embodiment, there may be also used electrosensitive recording paper, photosensitive recording medium, heat-sensitive recording paper, or pressure-sensitive recording paper. It is to be understood that the reading means should be selected in accordance with the properties of the recording medium used.

As for the sample supply containers and sample receptacles, they may be selected from such types as shown in FIGS. 2B to 2F. The container of FIG. 2B is a cylindrical container with a recording medium attached to the side face thereof. The container of FIG. 2C is a cylindrical container provided with a flat-sided member to which a recording medium is affixed. The container shown in FIG. 2D is a semicylindrical container, while the container of FIG. 2E is a square tube. Further, the container of FIG. 2F is a semicylindrical container with the lower portion tapered.

What we claim is:

1. A pipetting apparatus for automatic analyzer, comprising: a sample supply container holding a sample and provided with a recording medium; a means for writing sample information in said recording medium of said sample supply container and reading the written sample information; a first confirmation means for confirming the identity of the written information with the read information; a sample receptacle with a recording medium being conveyed so as to face said sample supply container storing said sample information; a means for reading the sample information recorded in said recording medium of said sample supply container and recording the read sample information in said recording medium of said sample receptacle; a second confirmation means for confirming the identity of the sample information recorded in said recording medium of said sample receptacle with the sample information recorded in said recording medium of said supply container; and a pipetting control unit for pipetting in response to the identical information from said second confirmation means.

2. A pipetting apparatus according to claim 1, wherein each said recording medium is a magnetic tape, and each said read-write means is formed of a magnetic head to come in contact with said magnetic tape for reading and writing of the sample information.

3. A pipetting apparatus according to claim 1, wherein said sample supply container and said sample receptacle are bottomed cylindrical containers each having a flat side affixed by said recording medium.

4. A pipetting apparatus according to claim 1, wherein said sample supply container and said sample receptacle are supported respectively by first and second conveyors disposed facing each other.

5. A pipetting apparatus, comprising: a plurality of sample supply containers each receiving a sample to be analyzed and having a recording medium; a first conveyor means for supporting and conveying said sample supply containers; a means for recording sample information in the recording medium of each corresponding sample supply container and reading the recorded sample information; a first confirmation means for confirming the identity of the read sample information with the recorded sample information; a plurality of sample receptacles each provided with a recording medium; a second conveyor means for supporting and conveying said sample receptacles opposite to said sample supply containers; a means for reading said sample information from the recording medium of said sample supply container in which said sample information is recorded and writing the read sample information in the recording medium of at least one of said sample receptacles; a second confirmation means for comparing the sample information written in said sample receptacle with the sample information read out from said recording medium of said sample supply container and confirming the identity thereof; a pipetting information memory means storing pipetting information; and a pipetting control unit for reading out the pipetting information from said pipetting information memory means in accordance with the identical information from said second confirmation means and the sample from said sample supply container to the corresponding sample receptacle in accordance with said pipetting information.

* * * * *